US006499361B1

(12) United States Patent
Costantino et al.

(10) Patent No.: US 6,499,361 B1
(45) Date of Patent: Dec. 31, 2002

(54) METHOD AND APPARATUS FOR UNIFORM SORBATE EQUILIBRATION OF SOLID SAMPLES

(75) Inventors: Henry R. Costantino, Grantham, NH (US); Josiah Brown, Somerville, MA (US)

(73) Assignee: Alkermes Controlled Therapeutics, Inc., Cambridge, MA (US)

( * ) Notice: Subject to any disclaimer, the term of this patent is extended or adjusted under 35 U.S.C. 154(b) by 0 days.

(21) Appl. No.: 09/507,238

(22) Filed: Feb. 18, 2000

(51) Int. Cl.[7] ............................................. G01N 1/00
(52) U.S. Cl. ........................................................ 73/863
(58) Field of Search ............................ 73/1.06, 1.07, 73/73, 863, 863.21, 866

(56) References Cited

U.S. PATENT DOCUMENTS

| | | | |
|---|---|---|---|
| 4,566,326 A | 1/1986 | Lowell | 73/432 |
| 4,924,601 A | 5/1990 | Bercaw | 34/46 |
| 5,000,624 A | 3/1991 | Steiger | 406/124 |
| 5,056,547 A | 10/1991 | Brownawell | 137/3 |
| 5,124,100 A | 6/1992 | Nishii et al. | 264/82 |
| 5,156,498 A | 10/1992 | Nomura et al. | 406/48 |
| 5,248,222 A | 9/1993 | Littman et al. | 406/142 |
| 5,266,492 A | 11/1993 | Wood et al. | 436/34 |
| 5,274,931 A | 1/1994 | Ogiri et al. | 34/46 |
| 5,340,541 A | 8/1994 | Jackson et al. | 422/75 |
| 5,526,581 A | 6/1996 | Winterson et al. | 34/474 |
| 5,685,192 A | 11/1997 | Shriner et al. | 73/73 |
| 5,712,421 A | 1/1998 | Raisanen | 73/19.01 |
| 5,715,611 A | 2/1998 | Jacobs et al. | 34/316 |
| 5,869,741 A * | 2/1999 | Scheppers et al. | 73/1.06 |

FOREIGN PATENT DOCUMENTS

| | | |
|---|---|---|
| EP | 0449 100 A2 | 10/1991 |
| JP | 10 332676 A | 12/1998 |

OTHER PUBLICATIONS

Young, J. F., "Humidity Control in the Laboratory Using Salt Solutions—A Review," *J. Appl. Chem.*, vol. 17:241–245 Sep. 1967.

Costantino, H. R., et al., "Determining the Water Sorption Monolayer of Lyophilized Pharmaceutical Proteins," *Journal of Pharmaceutical Sciences*, vol. 86(12)1390–1393 Dec. 1997.

Hsu, C. C., et al., "Determining the Optimum Residual Moisture in Lyophilized Protein Pharmaceuticals," *Develop. Biol. Standard*, vol. 74:255–271 1991 (With No Month Listed).

* cited by examiner

Primary Examiner—Robert R. Raevis
(74) Attorney, Agent, or Firm—Hamilton, Brook, Smith & Reynolds, P.C.

(57) ABSTRACT

Solid samples having a uniform sorbate content are produced by directing a gas having a constant sorbate pressure through a plurality of containers, each container enclosing a solid sample. The sorbate content of the solid samples equilibrates with the sorbate pressure in the gas, thereby causing the solid samples to have a uniform sorbate content. An apparatus that can be employed to generate solid samples having a uniform sorbate content includes a relative humidity generator, and a manifold which connects the relative humidity generator to a plurality of solid sample containers.

24 Claims, 1 Drawing Sheet

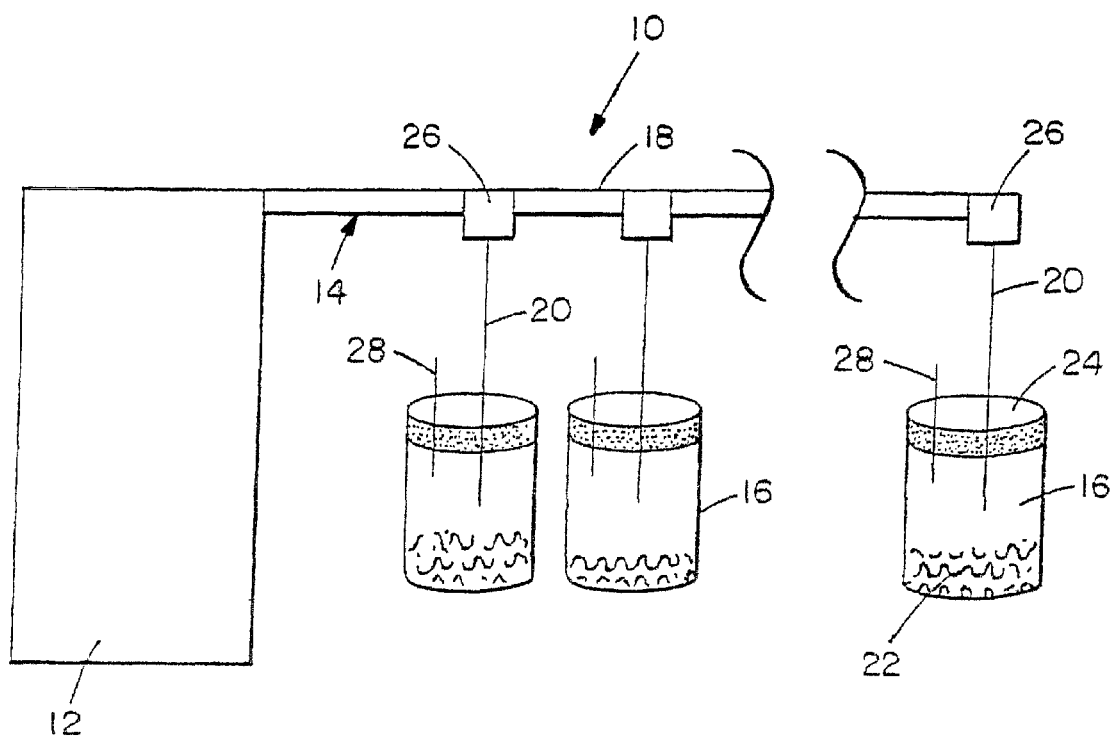

METHOD AND APPARATUS FOR UNIFORM SORBATE EQUILIBRATION OF SOLID SAMPLES

BACKGROUND OF THE INVENTION

Properties of powder materials can be affected by the amount of moisture they contain. Examples of such materials include pharmaceutical, chemical, food, agricultural and other products. To extend shelf life, many powders are formulated and stored under conditions that minimize moisture content and product degradation. For example, the residual moisture content of some lyophilized drugs and biologically active compounds needs to be carefully controlled so that their activity is maintained over their shelf or storage life. In order to study product stability, product degradation and other product properties affected by the amount of moisture present in the powder, manufacturers typically generate powder samples of known moisture content, and, after storing the samples for a period of time, test their properties.

Existing techniques for preparing powder samples of known moisture content often are cumbersome and time consuming. It is common, for example, to place a powder sample in a large chamber of a known relative humidity. In such a case, the time required to reach equilibrium between the sample and the chamber environment can be extensive. Transferring samples to and from the chamber can offset the relative humidity in the chamber environment as well as the moisture content of the sample. In addition, non-uniform conditions throughout the chamber may result in moisture content uncertainties in powder samples placed at different positions in the chamber.

One common approach for generating a chamber environment at a known relative humidity relies on using saturated salt solutions. Preparing saturated salt solutions requires careful laboratory work. In addition, since, for a given temperature a given saturated salt provides only one relative humidity, to generate samples of different moisture contents requires multiple experiments using different saturated salt solutions.

Therefore, a need exists for a method of producing powder samples having a specified moisture content which overcomes or minimizes the above-referenced problems.

SUMMARY OF THE INVENTION

The present invention is directed to a method and apparatus for producing a plurality of solid samples having a uniform sorbate content.

The method includes directing a gas which includes a sorbate at a constant sorbate pressure, through a plurality of containers, each container enclosing a solid sample. The sorbate content of the solid samples equilibrates with the sorbate pressure in the gas, thereby causing the solid samples to have a uniform sorbate content.

In one embodiment, the method includes enclosing a plurality of solid samples in separate containers and directing a gas stream having a constant sorbate pressure through said containers, whereby the sorbate content of the solid samples equilibrates with the sorbate pressure in the gas stream, thereby causing the solid samples to have a uniform sorbate content.

In another embodiment, the method includes correlating the sorbate content of solid samples with the sorbate pressure of a gas, whereby the sorbate content of the solid can be determined by regulating the sorbate pressure of the gas with which the solid is in equilibrium, generating a stream of gas having a constant sorbate pressure and directing the gas stream through a plurality of containers, each container enclosing a sample of the solid. The solid samples equilibrates with the sorbate pressure of the gas stream, resulting in powders that have a uniform sorbate content corresponding to the sorbate pressure in the gas stream.

The apparatus of the invention includes a source of gas having a constant sorbate pressure, a plurality of containers for enclosing solid samples, and a manifold extending from the source of gas to the containers.

In one embodiment, the apparatus includes a main conduit for connection to a relative humidity generator and a plurality of side conduits, each conduit being suitable for connection to a container.

This invention has many advantages. For example, it provides a rapid method for preparing multiple samples of uniform sorbate content. The method of the invention generally is less cumbersome and painstaking than conventional saturated salt solution techniques. For example, the same apparatus can be employed to generate a gas stream having any sorbate content. In addition, the method and apparatus of the invention typically do not require a large chamber for equilibrating powder samples with the chamber environment. Also, a plurality of solid samples having a desired sorbate content can be prepared simultaneously. Such samples can be used, for example, in moisture stability studies to determine optimal moisture levels for product integrity. Furthermore, the invention can be employed to generate solid samples having a substantially uniform sorbate content, such as uniform water content.

BRIEF DESCRIPTION OF THE DRAWINGS

The FIGURE is a schematic diagram of one embodiment of the apparatus of the invention.

DETAILED DESCRIPTION OF THE INVENTION

The foregoing and other objects, features and advantages of the invention will be apparent from the following more particular description of preferred embodiments of the invention, as illustrated in the accompanying drawing. The drawing is not necessarily to scale, emphasis instead being placed upon illustrating the principles of the invention.

The FIGURE is a schematic representation of one embodiment of the apparatus of the invention. It is to be understood that, although the method of the invention will be described with reference to the apparatus represented in the FIGURE, the method of the invention can be conducted by other suitable apparatus.

Shown in the FIGURE is apparatus 10, which includes relative humidity generator 12. Relative humidity generator 12 is employed to produce a gas having a constant sorbate pressure; in this embodiment the "sorbate" is water. In a preferred embodiment, relative humidity generator 12 generates a gas of essentially constant sorbate pressure by combining a carrier gas stream with a stream of saturated sorbate vapor. The carrier gas can be, for example, air, nitrogen, oxygen, carbon dioxide, argon and combinations thereof.

A "sorbate", as that term is employed herein, is a compound which can be adsorbed on the solid surface, absorbed into the solid, for instance through pores or interstices, or otherwise taken up by a solid material. The binding of the sorbate can range from relatively weak, for instance of the magnitude of van der Waals forces (i.e., physical adsorption resembling liquefaction), to relatively energetic, comparable to forces characterizing chemical compound formation (i.e., chemical adsorption or chemisorption). Examples of sorbates include, but are not limited to, water, volatile organic compounds, vapors generated by subliming solids and any combinations thereof. In a preferred embodiment, the sorbate is a solvent, a reactant or a reagent, employed during the manufacture of a solid material and which can be present as residue in the resulting solid material. The sorbate also can be a gas, such as, for example, oxygen, carbon monoxide, carbon dioxide, oxides of nitrogen, oxides of sulfur, methane, ethane, halogenated hydrocarbons and others. The content of a gas sorbate in the gas stream can be expressed, for example, in terms of mole or mass fraction in the gas stream, partial pressure, or, as used herein, simply as pressure.

Mass flow controllers regulate the mix of the two gas streams to produce a single stream of gas which has a desired constant sorbate pressure. For volatile compounds, constant sorbate pressure values can be conveniently expressed in terms of relative vapor pressures. As used herein, the phrase "relative vapor pressure" is the percent ratio between the actual vapor pressure of a compound in the gas and the saturation vapor pressure of that compound in the gas. For water, this ratio is referred to as relative humidity or RH.

Relative humidity generator 12 can be a commercial unit such as, for example, the Automated RH Generator Model RH-200, manufactured by VTI Corporation, Hialeah, Fla. In the case of water vapor, such a unit can produce a gas having a relative humidity ranging from about 0% to about 95%.

The gas generated by relative humidity generator 12 can be at room temperature or at another desired temperature. For example, the gas can be heated or cooled by heat exchange or by other means known to those skilled in the art.

In other emodiments of the invention, a gas having a constant sorbate pressure can be prepared by other techniques known in the art, such as, for example, by using saturated salt solutions or by conventional gas blending techniques.

The gas having a constant sorbate pressure is directed through manifold 14, into a plurality of containers 16. Manifold 14 can be constructed from materials such as glass, plastics, metals, combinations thereof or other materials. Materials that do not corrode or react when in contact with the carrier gases or vapors employed are preferred. Manifold 14 includes main conduit 18 connecting relative humidity generator 12 to side conduits 20. In turn, side conduits 20 connect main conduit 18 to containers 16. In one embodiment of the invention, side conduits 20 include needle gas inlets.

Containers 16 enclose solid samples 22. Containers 16 can be vials, test tubes, and other suitable types of sample holders. In a preferred embodiment, containers 16 are containers typically employed in the sale or end use of the solid. The number of containers 16 that can be connected to relative humidity generator 12 through manifold 14 can vary and can depend on the number of samples desired as well as on the physical dimensions of vapor equilibration apparatus 10. In a typical arrangement such as shown in the FIGURE, about ten containers 16 are connected to manifold 14. More than one manifold 14 can be connected to relative humidity generator 12, with each manifold 14 connecting relative humidity generator 12 to a plurality of containers 16.

Containers 16 can be constructed from glass, plastic, metal or other suitable materials. Preferably, containers 16 are fabricated from a material which is not corroded and does not react when contacted with solid sample 22 or with the gas having a constant sorbate pressure generated by relative humidity generator 12 and directed through manifold 14 into containers 16.

In one embodiment of the invention, the interior of containers 16 are isolated from the surrounding atmosphere by, for example, suitable means, such as septa 24. Valves 26 can be employed to regulate the flow of gas of constant sorbate pressure to containers 16. A preferred example of valve 26 is a three-way valve. To avoid pressure build-up apparatus 10 can be provided with means for pressure relief, for example needle gas outlets 28. Needle gas outlets 28 can include valves, not shown.

Each container 16 encloses a solid sample. Preferred solids include powers. As used herein, the term powder generally refers to particulate solids, granules, powder agglomerates, powder aggregates, tablets and other granular materials. The powders can be free flowing or well dispersed, caked or can include combinations of free flowing and caked portions. The powders can be crystalline or amorphous, can have various particle shapes, such as, for example, spherical, cylindrical, filament-like, irregular or can have any other shape. The method of the invention can be carried out with very fine, fine or coarse powders. Suitable particle sizes can range, for example, from about a few nanometers (nm) to about one centimeter (cm). Preferably, powder particles can range from about 100 nm to about 1 millimeter (mm).

Free flowing powders can be formed, for example, by spray drying, spray freeze drying, critical fluid precipitation, solvent induced or salt induced precipitation and drying or by milling following bulk freeze drying. Lyophilization, for example product lyophilization in vials, can result in caked powders.

Suitable solids also can include materials other than powders, such as, for example, gels, highly viscous materials, filaments, fibers, elastomers and other polymers. In a preferred embodiment, the solid is hygroscopic.

Suitable solids can include, but are not limited to: organic or inorganic chemical compounds, pharmaceuticals, foods, minerals, agricultural and biologically active compounds and many others. In one embodiment of the invention, the solid sample includes at least one compound suitable for being administered to a human or animal, such as, for example, a protein, peptide or polypeptide, enzyme, hormone, or some other therapeutic, prophylactic or diagnostic drugs or pharmaceutical formulation. Other suitable solid materials include, but are not limited to, small molecules, polysaccharides and other sugars, lipids, DNA, RNA, nucleic acid sequences, genes, antisense molecules, antigens and combinations thereof. Specific examples include but are not limited to insulin, growth hormones, interferons, erythropoietin and others. Suitable solids also include excipients such as those employed in pharmaceutical formulations. Examples include but are not limited to bulking agents, stabilizing agents and other inert materials known to those skilled in the art.

Initially, solid samples 22 in containers 16 can be under vacuum. Alternatively, the atmosphere in containers 16 can be air or an inert gas, such as, for example, nitrogen. Containers 16 enclosing solid samples 22 can be heated or cooled with the help of a temperature bath. Heating tape can also be employed as can other methods known to those skilled in the art. The temperature of solid samples 22 can be measured, for example by thermocouples, not shown in the FIGURE.

In one embodiment of the invention, solid samples 22 are initially dry. In another embodiment, solid samples 22 have an initial sorbate content which can be different from the uniform sorbate content of solid samples obtained by practicing the invention.

In a preferred embodiment, the constant sorbate pressure of the gas, that upon equilibrations will produce solid samples having the desired uniforn sorbate content, can be predicted from the sorption (or adsorption) isotherm of the sorbate/solid system of interest. Sorption iostherms typically are characteristic of a particular sorbate/solid system. For some sorbate/solid systems, sorption isotherms can be obtained from the published literature. Alternatively, sorption isotherms for a sorbate/solid system can be obtained experimentally. For example, such isotherms can be generated by adsorption/desorption methods, using the Brunauer-Emmett-Teller (BET) approach, as discussed, for example, by Hsu, C. C., et al. in *Develop. Biol. Standard.*, 74: 255–271 (1991) or by Costantino, H. R., et al. in *J. Pharm. Sci.*, 86(12): 1390–1393 (1997). A method and apparatus for generating moisture isotherms are also described in U.S. Pat. No. 5,685,192, issued on Nov. 11, 1997 to Shriner, et al. All these references are incorporated herein by reference in their entirety.

In one embodiment of the invention, the sorption isotherm for a particular sorbate/solid system is determined by using a gravimetric sorption analyzer. An example of such an apparatus is the Gravimetric Sorption Analyzer SGA-100, manufactured by VTI Corporation, Hialeah, Fla. The apparatus combines a relative humidity generator (such as discussed above) and a microbalance. The microbalance can be in a sealed chamber. A sample of the solid material of interest is placed on the balance; the chamber is sealed off and exposed to a stream of gas having a specific sorbate pressure or, in the case of a volatile compound, a relative sorbate vapor pressure. The sample is kept at a constant temperature and its weight loss or gain is measured over time. The weight change with respect to changes in sorbate pressure or relative sorbate vapor pressure can be measured and plotted.

Data correlating the sorbate content in the gas stream to the sorbate content in the solid material of interest are used to determine the sorbate pressure (which, in the case of volatile compounds can be expressed as relative sorbate vapor pressure and in the case of water as relative humidity) which, upon equilibration, will produce solid samples having the targeted sorbate content.

For some materials, the time required to reach equilibrium between the gas having a constant sorbate pressure and the solid samples is known or can be estimated by one skilled in the art. The time required to reach equilibrium can also be determined experimentally, as known in the art. In a preferred embodiment, it can be determined by employing a Gravimetric Sorption Analyzer as described above; equilibrium is reached when the weight of a solid sample no longer changes as a function of time. In many cases solid samples are found to equilibrates with the sorbate pressure in the gas stream in less than about 24 hours and often in less than about 2 hours.

Gas is directed through containers 16, thereby flushing the interior of containers 16 with the gas having a constant sorbate pressure. The flow of gas can be continuous or intermittent. Preferably, the gas volume of each container 16 is replaced at a rate in a range of up to about 1,000 volumes per minute.

As the gas is directed through containers 16, the sorbate content of the enclosed solid samples equilibrates, or reaches a steady state, with the pressure of the sorbate in the gas stream, thereby producing a plurality of solid samples having an uniform sorbate content. As used herein, solid samples having a uniform sorbate content refer to solid samples which have essentially the same sorbent content.

Gas is directed through containers 16 for a period of time sufficient to cause the sorbate content of the gas and that of samples 22 essentially to equilibrates. Typically, the period of time required to reach equilibrium is in a range of between about 1 hour and about 24 hours.

Following equilibration, containers 16 are sealed by closing valves 26 at side conduits 20 and sealing needle gas outlets 28. Sample containers 16 then can be removed for storage, testing and/or use.

Optionally, the sorbate content of the samples is measured to confirm that the target content has been obtained, or to ensure that the sorbate content among the samples essentially is uniform. Methods of measuring sorbate content in a solid sample are known in the art and include, for example, gravimetric, Karl Fischer titration, infrared spectroscopy and other suitable techniques. In a preferred embodiment, sorbate content of the solid samples is assayed by a gravimetric sorption analyzer, such as described below.

The invention will be further illustrated through the following examples which are not intended to be limiting.

EXEMPLIFICATION

EXAMPLE 1

Three sets of protein powder samples were prepared by the method of the invention. The target moisture content of the protein powder samples were of 7%, 9% and 15%. The protein selected was lyophilized human growth hormone (hGH). The apparatus was similar to that shown in the FIGURE and included Automated RH generator, Model RH-200. Also prepared were two sets of sustained release encapsulated hGH samples including a biocompatible polymeric material, as described, for example, in U.S. Pat. No. 5,654,010, issued on Aug. 5, 1997 to Johnson et al. and U.S. Pat. No. 5,891,478, issued on Apr. 6, 1999 to Johnson et al., the entire teachings of which are incorporated herein by reference.

Data correlating the solid sample moisture content and the gas relative humidity are shown in Table 1.

TABLE 1

Correlation of Relative Humidity with Moisture Content of hGH Protein Powder and Encapsulated hGH Material

| Sample | % RH | Target Moisture Content |
|---|---|---|
| hGH | 40% | 7% |
| hGH | 50% | 9% |
| hGH | 70% | 15% |
| encapsulated hGH | 70% | 3% |
| encapsulated hGH | 85% | 5% |

Samples of hGH protein powder, or of sustained release encapsulated hGH, from the same lot were weighed out (approximately 3 to 5 mg per sample) into 1 ml injection vials, sealed with septa and crimped to form an airtight seal. Two needles (18G) were inserted into each sealed vial. One needle was attached to the multi-valve gas manifold system which had Luer-Lock connections. The other needle was left open to the air. This allowed for gas flow from the manifold system, into the vial, and out into the atmosphere. Thus, the interiors of the vials were flushed with the incoming gas of constant sorbate pressure.

A gas manifold system and the vials were then attached to the gas outlet stream of the automated relative humidity (RH) generator. The RH generator was set to generate gas having the constant relative humidity, selected to correspond to the specific moisture uptake by the protein powder or by the sustained release encapsulated hGH samples. At least two hours were allowed to reach equilibrium between the solid samples and the gas of constant relative humidity. The specific moisture content of the protein powder samples was assayed by using the gravimetric sorption analyzer (GSA). (The model used was SGA-100TR, manufactured by VTI Corporation.) Three sets of 10 protein powder samples were generated along with two sets of 10 encapsulated hGH samples. Table 2 shows the target moisture content and the average of the actual moisture content achieved by the samples in each set.

TABLE 2

Moisture Content of hGH Protein Powder Samples and of Encapsulated hGH Samples

| Sample | % RH | Target Moisture Content | Measured Moisture Content* |
|---|---|---|---|
| hGH | 40% | 7% | 6.9 ± 0.03% |
| hGH | 50% | 9% | 7.9 ± 0.1% |
| hGH | 70% | 15% | 15.4 ± 0.7% |
| encapsulated hGH | 70% | 3% | 2.7 ± 0.1% |
| encapsulated hGH | 85% | 5% | 3.8% |

*samples assayed in duplicate by GSA.

Differences in moisture content between the sample in the container nearest the relative humidity generator (Sample #1) and the sample in the container farthest from the humidity generator (Sample #10) are shown in Table 3.

TABLE 3

Sample Uniformity Measurements

| Sample | % RH | $H_2O$ | Moisture Content Sample #1 | Moisture Content Sample #10 | Average Moisture Content | Std. Dev. |
|---|---|---|---|---|---|---|
| hGH | 40% | 7% | 6.9 | 6.8 | 6.9 | 0.0 |
| hGH | 50% | 9% | 7.8 | 8.0 | 7.9 | 0.1 |
| hGH | 70% | 15% | 14.9 | 15.9 | 15.4 | 0.4 |

EQUIVALENTS

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method for producing a plurality of solid samples having a uniform sorbate content, comprising directing gas from a gas stream including a sorbate and having a constant sorbate pressure, through a plurality of containers, each container enclosing a solid sample, whereby the sorbate content of the solid samples equilibrates with the sorbate pressure in the gas stream, thereby causing said solid samples to have a uniform sorbate content.

2. The method of claim 1, further including the step of generating the gas stream.

3. The method of claim 2, further including the step of correlating the sorbate content of the samples with the sorbate pressure in the gas stream, whereby sorbate content of the samples can be determined by regulating the sorbate pressure in the gas stream.

4. The method of claim 3, wherein the sorbate content of the samples is correlated to the sorbate pressure in the gas stream.

5. The method of claim 1, wherein the gas includes air.

6. The method of claim 1, wherein the gas includes nitrogen.

7. The method of claim 1 wherein the solid includes a powder.

8. The method of claim 1 wherein the solid includes a caked material.

9. The method of claim 1, wherein the sample includes a biologically active compound.

10. The method of claim 9, wherein the sample includes human growth hormone.

11. The method of claim 1, wherein the sorbate includes a volatile organic compound.

12. The method of claim 1 wherein the sorbate includes water.

13. The method of claim 1 wherein the sorbate includes a gas and wherein said sorbate pressure is the partial pressure of the sorbate gas in the gas stream.

14. A method for producing a plurality of solid samples having a uniform sorbate content, comprising the steps of:

a) enclosing a plurality of solid samples in separate containers; and b) directing gas from a gas stream including a sorbate and having a constant sorbate pressure through said containers, whereby sorbate content of the solid samples equilibrates with the sorbate pressure in the gas stream, thereby causing said solid samples to have a uniform sorbate content.

15. A method for producing a plurality of solid samples having a uniform sorbate content, comprising the steps of:

a) correlating the sorbate content of solid samples with the sorbate pressure of a gas, whereby the sorbate content of the solid can be determined by regulating the sorbate pressure with which the solid is in equilibrium;

b) generating a stream of said gas, said gas stream having a constant sorbate pressure; and c) directing gas from said gas stream through a plurality of containers, each container enclosing a sample of said solid, whereby sorbate content of the solid samples equilibrates with the sorbate pressure of the gas stream, thereby causing the solid samples to have a uniform sorbate content corresponding to the sorbate pressure in the gas stream.

16. An apparatus for producing a plurality of solid samples having a uniform sorbate content, comprising:

a) a source of gas including a sorbate and having a constant sorbate pressure;

b) a plurality of containers for enclosing said solid samples;

c) a manifold extending from the source of gas to the containers; and d) means for discharging gas from the containers, thereby causing gas directed from said source of gas to be directed through the containers.

17. The apparatus of claim 16, wherein the source of gas includes a relative humidity generator.

18. The apparatus of claim 16, further including means for controlling the temperature of the containers.

19. The apparatus of claim 16, wherein the containers are connected in parallel.

20. The apparatus of claim 16, further including at least one valve at the manifold, whereby gas flow to at least one of said containers can be regulated by said valve.

21. The apparatus of claim 20 wherein said valve is a three-way valve.

22. An apparatus for preparing solid samples having a specified sorbate content, comprising:
   a) a main conduit for connection to a relative humidity generator;
   b) a plurality of side conduits that extend from the main conduit, each conduit being suitable for connection to a container; and
   c) means for discharging gas from the containers.

23. The apparatus of claim 22, including a valve at a side conduit, whereby gas flow through said side conduit can be regulated by said valve.

24. The apparatus of claim 23, wherein said valve is a three-way valve.

* * * * *